United States Patent
Taylor et al.

(10) Patent No.: US 10,610,273 B2
(45) Date of Patent: Apr. 7, 2020

(54) BONE PLATE WITH TRANSVERSE SCREW

(71) Applicant: In2Bones USA, LLC, Memphis, TN (US)

(72) Inventors: Alan G. Taylor, Memphis, TN (US); Rebecca Hawkins Wahl, Escondido, CA (US); Casey Chambers, Memphis, TN (US)

(73) Assignee: In2Bones USA, LLC, Memphis, TN (US)

( * ) Notice: Subject to any disclaimer, the term of this patent is extended or adjusted under 35 U.S.C. 154(b) by 226 days.

(21) Appl. No.: 15/795,039

(22) Filed: Oct. 26, 2017

(65) Prior Publication Data

US 2018/0125548 A1 May 10, 2018

Related U.S. Application Data

(60) Provisional application No. 62/418,677, filed on Nov. 7, 2016.

(51) Int. Cl.
*A61B 17/80* (2006.01)

(52) U.S. Cl.
CPC ...... *A61B 17/8014* (2013.01); *A61B 17/8057* (2013.01); *A61B 17/8061* (2013.01)

(58) Field of Classification Search
CPC . A61B 17/80; A61B 17/8004; A61B 17/8014; A61B 17/8052; A61B 17/8057; A61B 17/8061
See application file for complete search history.

(56) References Cited

U.S. PATENT DOCUMENTS

| | | | | | |
|---|---|---|---|---|---|
| 4,408,601 | A | * | 10/1983 | Wenk | A61B 17/8014 606/282 |
| 4,493,317 | A | * | 1/1985 | Klaue | A61B 17/8014 606/282 |
| 5,693,055 | A | * | 12/1997 | Zahiri | A61B 17/8061 606/305 |
| 6,309,393 | B1 | * | 10/2001 | Tepic | A61B 17/80 606/280 |
| 9,060,822 | B2 | * | 6/2015 | Lewis | A61B 17/8014 |
| 9,545,276 | B2 | * | 1/2017 | Buchanan | A61B 17/8061 |
| 9,907,588 | B2 | * | 3/2018 | Parekh | A61B 17/8014 |
| 10,213,236 | B2 | * | 2/2019 | Lewis | A61B 17/8014 |
| 2004/0034356 | A1 | * | 2/2004 | LeHuec | A61B 17/1728 606/914 |

(Continued)

*Primary Examiner* — Eric S Gibson
(74) *Attorney, Agent, or Firm* — Rutan & Tucker LLP; Hani Z. Sayed

(57) ABSTRACT

An apparatus for a bone fusion assembly is provided for compressing adjacent bones across a bone fusion site to encourage fusion thereof. The bone fusion assembly includes a generally elongate member comprising a plate that has one or more fixation apertures to receive fasteners that are configured to be coupled with the adjacent bones. A threaded fastener comprising a bone screw, including a head portion and a shank, is configured to traverse the bone fusion site. A slanted aperture disposed in the plate is configured to receive the bone screw at a predetermined angle with respect to a plane of the plate. The slanted aperture comprises a smooth countersunk surface and one or more teeth that are configured to cooperate with the head portion of the bone screw to compress the adjacent bones together and encourage bone fusion therebetween.

8 Claims, 4 Drawing Sheets

(56) References Cited

U.S. PATENT DOCUMENTS

| | | | |
|---|---|---|---|
| 2007/0233106 A1* | 10/2007 | Horan | A61B 17/8061 606/282 |
| 2008/0051786 A1* | 2/2008 | Jensen | A61B 17/8057 606/86 A |
| 2008/0140130 A1* | 6/2008 | Chan | A61B 17/1728 606/280 |
| 2009/0024172 A1* | 1/2009 | Pizzicara | A61B 17/8014 606/280 |
| 2009/0171399 A1* | 7/2009 | White | A61B 17/80 606/286 |
| 2009/0210010 A1* | 8/2009 | Strnad | A61B 17/8014 606/280 |
| 2010/0125300 A1* | 5/2010 | Blitz | A61B 17/8061 606/281 |
| 2010/0256687 A1* | 10/2010 | Neufeld | A61B 17/80 606/289 |
| 2010/0274293 A1* | 10/2010 | Terrill | A61B 17/8057 606/286 |
| 2011/0009866 A1* | 1/2011 | Johnson | A61B 17/1728 606/70 |
| 2011/0264149 A1* | 10/2011 | Pappalardo | A61B 17/8019 606/286 |
| 2011/0295324 A1* | 12/2011 | Donley | A61N 17/8014 606/289 |
| 2012/0065689 A1* | 3/2012 | Prasad | A61B 17/8061 606/286 |
| 2012/0136398 A1* | 5/2012 | Mobasser | A61B 17/863 606/311 |
| 2012/0209334 A1* | 8/2012 | Lewis | A61B 17/8014 606/286 |
| 2013/0158608 A1* | 6/2013 | Viola | A61B 17/80 606/289 |
| 2013/0172942 A1* | 7/2013 | Lewis | A61B 17/8014 606/281 |
| 2014/0148859 A1* | 5/2014 | Taylor | A61B 17/8061 606/282 |
| 2014/0277176 A1* | 9/2014 | Buchanan | A61B 17/8061 606/281 |
| 2015/0223851 A1* | 8/2015 | Hill | A61B 17/8004 606/281 |
| 2015/0272639 A1* | 10/2015 | Lewis | A61B 17/8014 606/282 |
| 2016/0256204 A1* | 9/2016 | Patel | A61B 17/8014 |
| 2017/0238978 A1* | 8/2017 | Lewis | A61B 17/8014 |
| 2018/0049785 A1* | 2/2018 | Langdale | A61B 17/8042 |
| 2018/0125548 A1* | 5/2018 | Taylor | A61B 17/8014 |
| 2019/0150994 A1* | 5/2019 | Lewis | A61B 17/8014 |

* cited by examiner

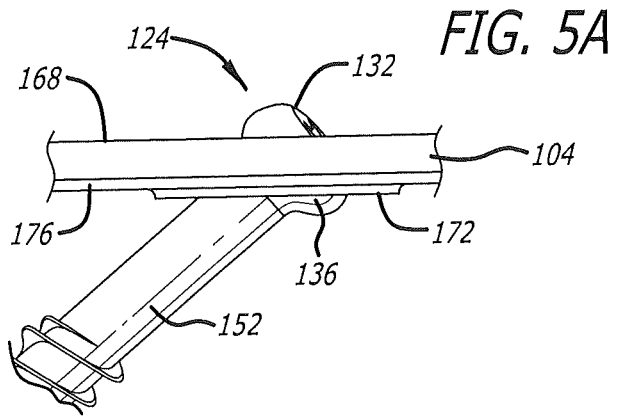
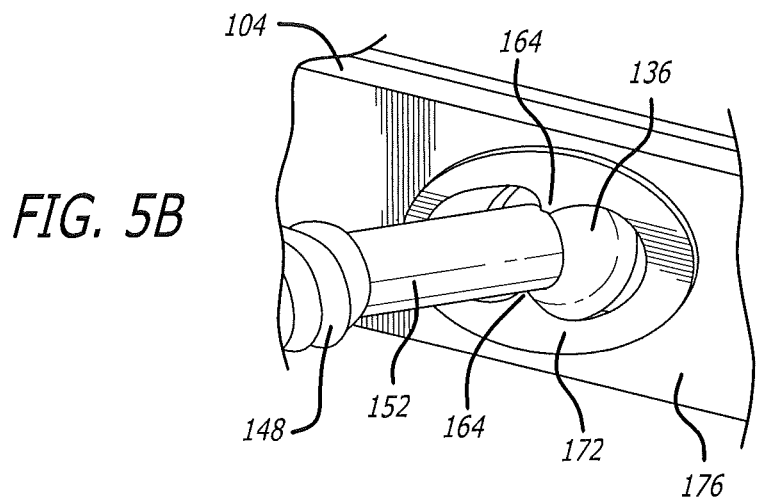
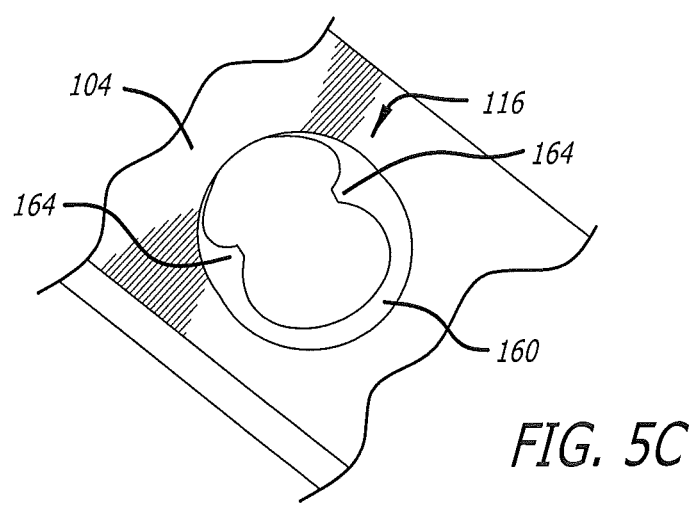

BONE PLATE WITH TRANSVERSE SCREW

PRIORITY

This application claims the benefit of and priority to U.S. Provisional Application, entitled "Bone Plate With Transverse Screw," filed on Nov. 7, 2016 and having application Ser. No. 62/418,677.

FIELD

The field of the present disclosure generally relates to securing bones together. More particularly, the field of the invention relates to an apparatus for fusing and compressing bones of the human body.

BACKGROUND

A fusion bone plate implant may be utilized in conjunction with one or more fasteners so as to generate compression and stability at a bone interface. An implant coupled with fasteners generally serves to stabilize bones, or bone parts, relative to one another so as to promote bone fusion. In many applications, bone plates and fasteners are used to fuse bones, or bone parts, of the human body, such as bones in the foot, the ankle, the hand, the wrist, as well as various other portions of the body. Furthermore, during the course of certain medical procedures, a surgeon may immobilize one or more bones or the bone fragments by stabilizing the bones together in a configuration which approximates the natural anatomy. To this end, the surgeon may use fasteners to attach the bones to a bone plate implant so as to hold the bones in alignment with one another while they fuse together.

SUMMARY

An apparatus for a bone fusion assembly is provided for compressing adjacent bones across a bone fusion site to encourage fusion thereof. The bone fusion assembly includes an elongate member comprising a plate made of a semi-rigid material possessing a tensile strength suitable for immobilizing the adjacent bones. The plate includes one or more fixation apertures to receive fasteners that are configured to be coupled with the adjacent bones. The plate may be implemented with one or more directions of curvature, such that the plate matches an anatomical shape of the adjacent bones. The bone fusion assembly further includes a threaded fastener comprising a bone screw, having a head portion and a shank, that is configured to traverse the bone fusion site. The shank is comprised of distal threads and a proximal smooth portion. The distal threads are configured to rotatably engage within a suitably sized hole drilled across the bone fusion site, and the proximal smooth portion is configured to pass through the bone with relatively little resistance. A slanted aperture is disposed in the plate and configured to receive the bone screw at a predetermined angle with respect to a plane of the plate. The slanted aperture comprises a smooth countersunk surface and one or more teeth that are configured to cooperate with the head portion of the bone screw to compress the adjacent bones.

In an exemplary embodiment, a bone fusion assembly for compressing adjacent bones across a bone fusion site to encourage fusion thereof comprises an elongate member comprising a plate that includes one or more fixation apertures to receive fasteners that are configured to be coupled with the adjacent bones; a threaded fastener comprising a bone screw that includes a head portion and a shank, the bone screw being configured to traverse the bone fusion site; and a slanted aperture disposed in the plate and configured to receive the bone screw at a predetermined angle with respect to a plane of the plate, the slanted aperture comprising a smooth countersunk surface and one or more teeth configured to cooperate with the head portion to compress the adjacent bones.

In another exemplary embodiment, the one or more fixation apertures are configured to orient the fasteners substantially perpendicular to the plane of the plate. In another exemplary embodiment, the plate is implemented with one or more directions of curvature, such that the plate matches an anatomical shape of the adjacent bones. In another exemplary embodiment, the one or more directions of curvature cause the fasteners to be oriented in the adjacent bones at differing angles with respect to one another.

In another exemplary embodiment, the plate is comprised of a semi-rigid material, such as a biocompatible metal or PEEK, possessing a tensile strength suitable for immobilizing the adjacent bones. In another exemplary embodiment, the predetermined angle is an oblique angle that is selected to direct the bone screw across the bone fusion site and compress the adjacent bones together. In another exemplary embodiment, the predetermined angle ranges between substantially 35 degrees and substantially 45 degrees.

In another exemplary embodiment, the smooth countersunk surface and the one or more teeth are configured to slidably engage with an inferior end of the head portion during tightening of the bone screw into the adjacent bones. In another exemplary embodiment, the smooth countersunk surface and the one or more teeth are configured to cooperate with a maximal circumference of the head portion, such that a minimal portion of the head portion remains extending above an upper surface of the plate. In another exemplary embodiment, the maximal circumference is disposed between a superior end and an inferior end of the head portion.

In another exemplary embodiment, the shank is comprised of distal threads and a proximal smooth portion, the distal threads being configured to rotatably engage within a suitably sized hole drilled in the adjacent bones, and the proximal smooth portion being configured to pass through the bone with relatively little resistance. In another exemplary embodiment, the head portion is comprised of a superior end and an inferior end, the superior end including a shaped opening configured to engagedly receive a tool suitable for driving the bone screw into the suitably sized hole, and the inferior end being configured to be received within the slanted aperture such that the head portion countersinks within the slanted aperture and presses the plate against a surface of the adjacent bones. In another exemplary embodiment, a raised portion is disposed around the slanted aperture on an underside of the plate, the raised portion being a relatively thicker region of the plate that is configured to provide structural support to the plate and reduce an area of contact between the plate and the adjacent bones. In another exemplary embodiment, a raised portion is disposed around each of the one or more fixation apertures. In another exemplary embodiment, each of the raised portions disposed around the one or more fixation apertures has a thickness that is substantially the same as the thickness of the raised portion disposed around the slanted aperture.

In an exemplary embodiment, a bone screw for compressing adjacent bones across a bone fusion site comprises a head portion comprising a superior end and an inferior end; a shaped opening disposed within the superior end and configured to engagedly receive a tool for driving the bone screw into a hole drilled across the fusion site; a shank extending from the inferior end, the shank comprising distal threads and a proximal smooth portion; and a distal end configured to be advanced within the hole.

In another exemplary embodiment, the shaped opening is substantially concentric with a longitudinal axis of the shank and comprises a multi-lobe shape suitable to receive the tool. In another exemplary embodiment, the inferior end is configured to be received within a slanted aperture of a bone plate, such that the head portion countersinks within the slanted aperture and presses the bone plate against the surface of the adjacent bones. In another exemplary embodiment, a maximal circumference of the head portion is disposed between the superior end and the inferior ends so as to minimize protrusion of the head portion above an upper surface of the bone plate.

In another exemplary embodiment, the distal threads are configured to rotatably engage within the hole, and wherein the proximal smooth portion is configured to pass through the bone with relatively little resistance, the smooth portion being configured to allow the bone fusion site to close as the adjacent bones are compressed together. In another exemplary embodiment, the distal end includes one or more shapes that are configured to minimize resistance to forward movement of the bone screw within the hole drilled in the adjacent bones. In another exemplary embodiment, the distal end comprises one or more flutes that spiral along a portion of the distal threads and are configured to clean an interior of the hole and remove bone debris therefrom.

BRIEF DESCRIPTION OF THE DRAWINGS

The drawings refer to embodiments of the present disclosure in which:

FIG. 4A illustrates an isometric view of an exemplary embodiment of a bone screw that is configured to be coupled with a bone fusion plate for repairing bone fractures, fixating osteotomies, joining fusions of the skeletal system, and the like;

FIG. 5A illustrates a side plan view of the exemplary embodiment of the bone screw of FIG. 4A and FIG. 4B disposed at an oblique angle within an exemplary bone fusion plate;

FIG. 5B illustrates a lower isometric view of the exemplary embodiment of the bone screw of FIG. 4A and FIG. 4B disposed within the exemplary bone fusion plate shown in FIG. 5A; and FIG. 5C illustrates a top view of an exemplary embodiment of a slanted aperture disposed within the exemplary bone fusion plate shown in FIG. 5A and FIG. 5B.

Figure 1:
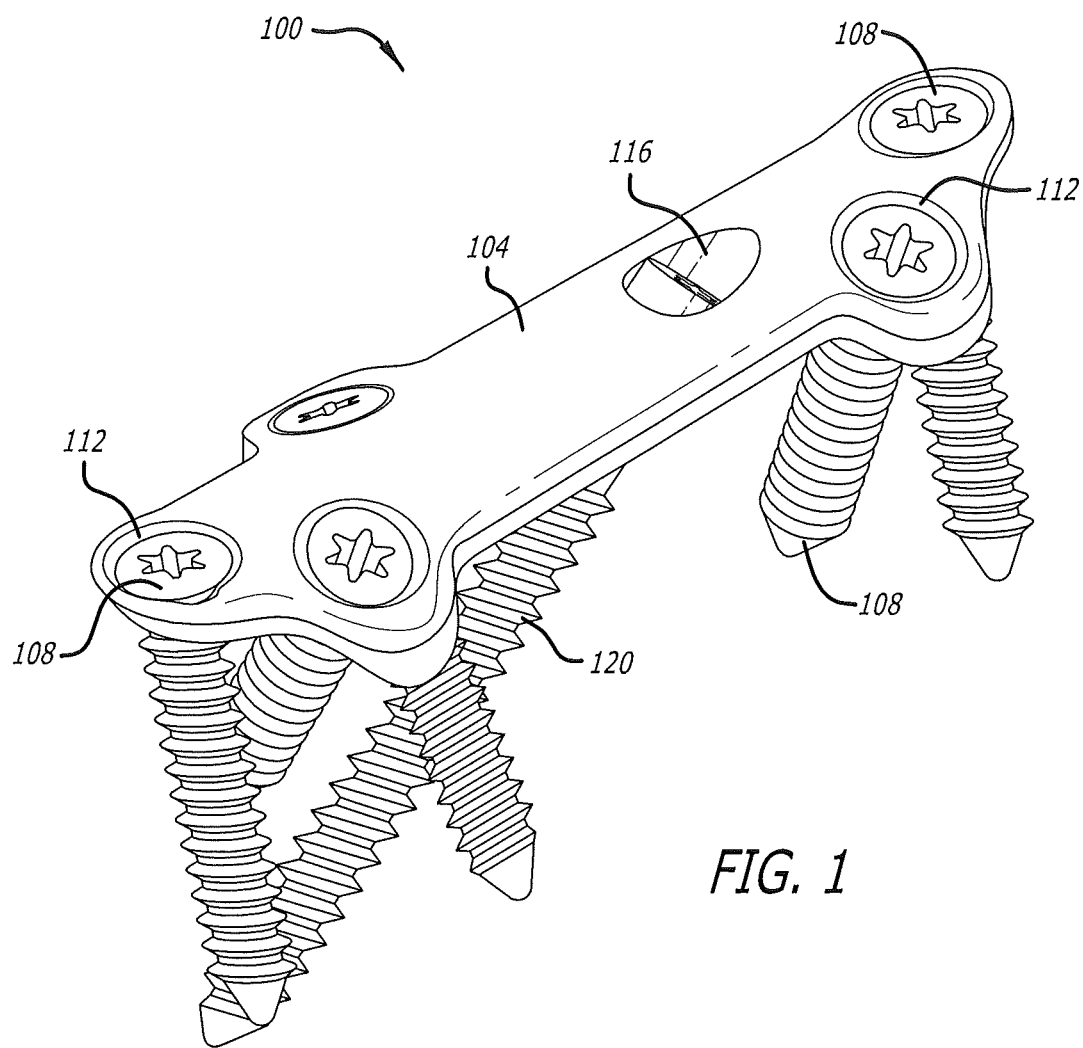
FIG. 1 illustrates an isometric view of an exemplary embodiment of a bone fusion assembly that is configured to fixate adjacent bones so as to encourage bone fusion.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first screw," may be made. However, the specific numeric reference should not be interpreted as a literal sequential order but rather interpreted that the "first screw" is different than a "second screw." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus for a bone fusion assembly configured to compress adjacent bones across a bone fusion site to encourage fusion thereof. The bone fusion assembly includes a generally elongate member comprising a plate that has one or more fixation apertures to receive fasteners that are configured to be coupled with the adjacent bones. A threaded fastener comprising a bone screw, including a head portion and a shank, is configured to traverse the bone fusion site. A slanted aperture disposed in the plate is configured to receive the bone screw at a predetermined angle with respect to a plane of the plate. The predetermined angle may be an oblique angle that is selected to suitably orient the bone screw across the bone fusion site. In some embodiments, the predetermined angle ranges between substantially 35 degrees and 45 degrees with respect to the plate of the plate. The slanted aperture comprises a smooth countersunk surface and one or more teeth that are configured to cooperate with the head portion of the bone screw to compress the adjacent bones together and encourage bone fusion therebetween. The smooth countersunk surface and the one or more teeth cooperate with the head portion such that a minimal extension of the head portion above an upper surface of the plate remains once the bone screw is tightened into the adjacent bones.

Figure 2:
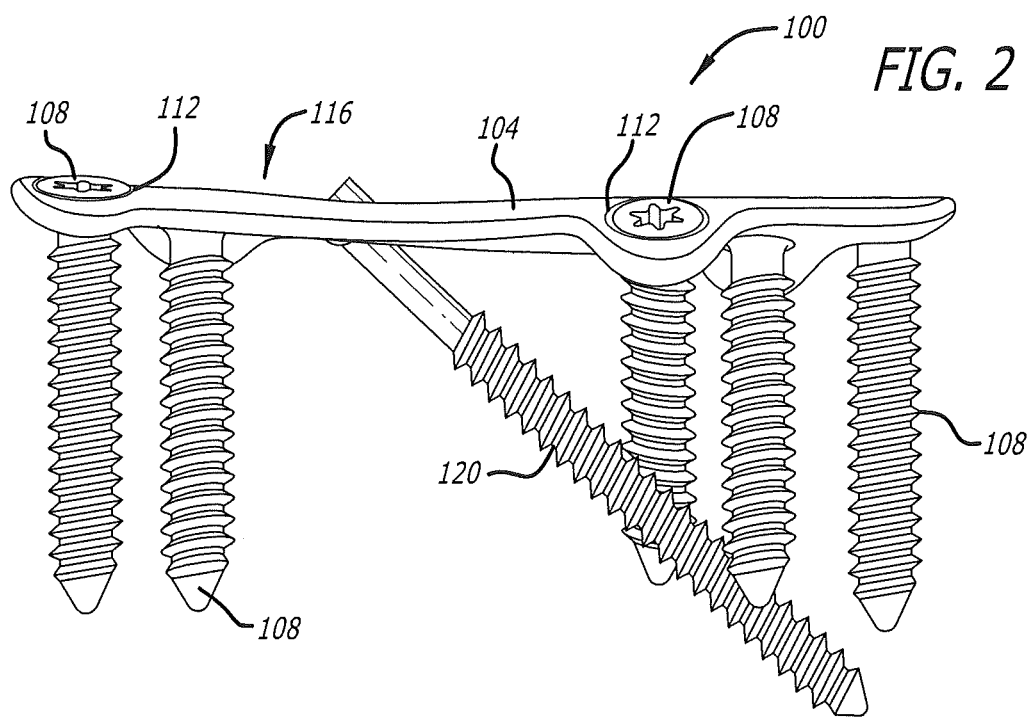
FIG. 2 illustrates a side plan view of the exemplary embodiment of the bone fusion assembly shown in FIG. 1.
Figure 3:
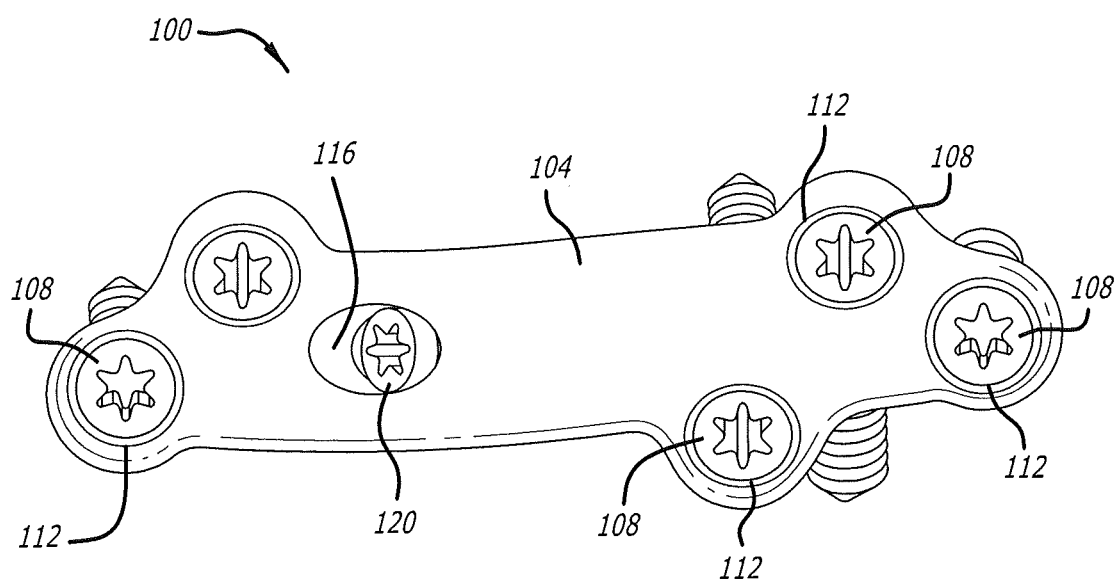
FIG. 3 illustrates a top plan view of the exemplary embodiment of the bone fusion assembly shown in FIG. 1.

FIGS. 1-3 illustrate an exemplary embodiment of a bone fusion assembly 100 comprising a plate 104 that is configured to be coupled with adjacent bones, across a bone fusion site, so as to fixate the bones and encourage fusion of the bones. The bone fusion assembly 100 may be advantageously used for repairing bone fractures, fixating osteotomies, joining fusions of the skeletal system, and the like. The plate 104 comprises a generally elongate member having multiple fixation apertures 112 that are configured to receive fasteners 108 such that the fasteners may be coupled with the adjacent bones on opposite sides of a bone fusion site, such as a bone fracture to be fused. The fixation apertures 112 are configured to orient the fasteners 108 substantially perpendicular to a plane of the plate 104. The plate 104 may be implemented with one or more directions, or degrees, of curvature such that the plate matches an anatomical shape of a target bone to which the bone fusion assembly 100 is to be coupled. For example, the plate 104 may be curved in a longitudinal direction and/or a lateral direction, without limitation. As shown in FIGS. 1-3, the curvature of the plate 104 may cause the fasteners 108 to be directed into the target bone at differing angles with respect to one another. The plate 104 may be comprised of a semi-rigid material, such as a biocompatible metal or PEEK, possessing a tensile strength suitable for immobilizing adjacent bone parts of the human body.

As best illustrated in FIGS. 1 and 3, the plate 104 comprises a slanted aperture 116 that is configured to receive a threaded fastener 120 at a predetermined angle with respect to the plane of the plate 104. In some embodiments, the predetermined angle may be any oblique angle that facilitates compressing the adjacent bones together by way of the threaded fastener 120 so as to encourage bone fusion. The oblique angle may range between substantially 35 degrees and 45 degrees with respect to the plane of the plate 104, without limitation.

Figure 4A:
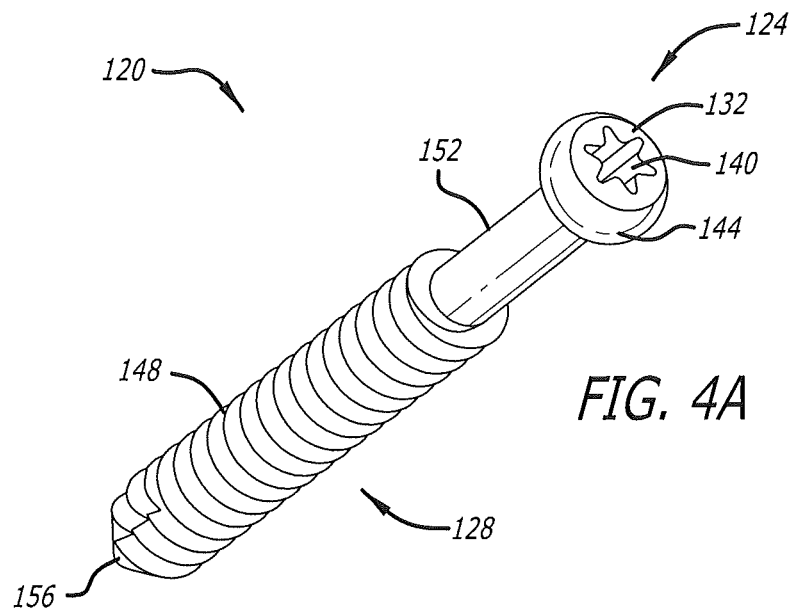
Figure 4B:
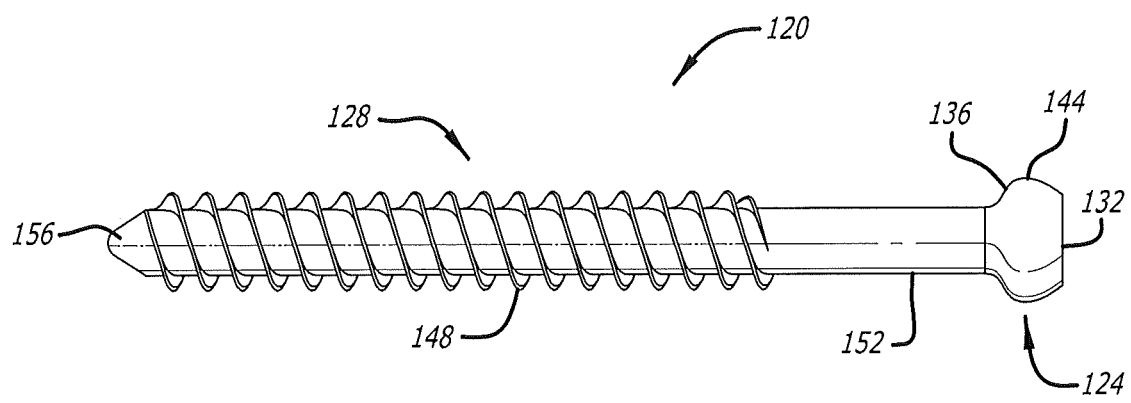
FIG. 4B illustrates a side plan view of the exemplary embodiment of the bone screw of FIG. 4A.

The threaded fastener 120 may be any component of hardware having a head configured to abut the surface of bone plate 104 and a shaft configured to secure bones together in a fixed configuration. In some embodiments, the threaded fastener 120 may comprise a bone screw, or other similar fastener suitable for use in bone. In some embodiments, the threaded fastener 120 may comprise a lag screw which includes a head that is rounded or tapered and coupled to a shaft having an unthreaded portion adjacent to the head and a threaded portion that ends at a distal tip. FIGS. 4A-4B illustrate an exemplary embodiment of a bone screw 120 that may be advantageously used with the plate 104 for repairing bone fractures, fixating osteotomies, joining fusions of the skeletal system, and the like. It should be understood that the terms "bone screw," "fastener," "fixator," and "screw" may be used interchangeably herein as they essentially describe the same type of device.

The bone screw 120 generally is an elongate member comprised of a head portion 124 and a shank 128. The head portion 124 is comprised of a superior end 132 and an inferior end 136. As best illustrated in FIG. 4A, the superior end 120 may include a shaped opening 140 that is substantially concentric with a longitudinal axis of the shank 128. The shaped opening 140 may be configured to engagedly receive a tool suitable for driving the bone screw 120 into a hole drilled in a patient's bone. Although in the illustrated embodiment, the shaped opening 140 is comprised of a hexalobe shape, any of various multi-lobe shapes, as well as other polygonal shapes, are also contemplated.

The inferior end 136 preferably is configured to be received within the slanted aperture 116, such that a majority of the head portion 124 countersinks within the slanted aperture and presses the plate 104 against the surface of the patient's bone. Further, a maximal circumference 144 of the head portion 124 may be disposed between the superior and inferior ends 132, 136, such as substantially midway between the superior and inferior ends, so as to minimize protrusion of the head portion 124 above an upper surface of the plate 104, as best shown in FIG. 5A. As will be appreciated, limiting protrusion of the head portion 104 above the plate 104 advantageously minimizes irritation to nearby soft tissue that may otherwise occur due to a relatively greater presence of the head portion 124.

As best shown in FIG. 4B, the shank 128 is comprised of distal threads 148 and a proximal smooth portion 152. The distal threads 148 are configured to rotatably engage within a suitably sized hole drilled in the patient's bone. Thus, turning the bone screw 100 in an appropriate direction by way of a tool coupled with the shaped opening 140, drives the distal threads 148 to engage with bone tissue surrounding the bone hole, advancing a distal end 156 of the bone screw 100 deeper into the bone hole and across a bone fracture to be fused. The proximal smooth portion 152 is configured to pass through the bone hole with relatively little resistance. Continued turning of the bone screw 100 then countersinks the inferior end 136 into the slanted aperture 116, drawing a majority of the head portion 124 beneath the upper surface of the plate 104. Upon tightening the bone screw 120 into the bone, the distal threads 148 push the bone portion near the distal threads toward the bone portion near the smooth portion 152 and the plate 124. The smooth portion 152 allows the fracture to close as the adjacent bone portions are compressed together.

It is contemplated that the bone screw 120 may be particularly well suited for compressing bone fractures, fixating osteotomies, joining fusions, as well as any other surgical procedure wherein compressing two adjacent bone portions is desired, without limitation. As will be appreciated, the bone screw 120 may be implemented in any of various lengths and diameters so as to advantageously repair a wide variety of differently sized and shaped bones within the human body. Furthermore, it is envisioned that the bone screw 120 may be configured for use in a veterinary capacity, and thus the bone screw may be implemented with various shapes and sizes that are suitable for use in different types of animals.

In some embodiments, the distal end 156 may include one or more shapes, such as a rounded portion and a tapered diameter, that are configured to minimize resistance to forward movement of the bone screw 120 within the interior of the bone hole. Further, one or more flutes may be incorporated into the distal end 156 and spiral along a portion of the distal threads 148. It is contemplated that the flutes may be configured to advantageously clean the interior of the bone hole and increase the diameter of the hole to accept the distal threads 148 of the advancing bone screw 120. As will be appreciated, the flutes may be configured with a spiral, or a rate of twist, that provides a desired rate of bone debris removal from the interior of the bone hole during rotation of the bone screw 120. It is contemplated that the one or more flutes may be implemented with any of various spirals without deviating beyond the spirit and scope of the present disclosure.

FIGS. 5A-5B illustrate an exemplary embodiment of the bone screw 120 disposed at an oblique angle within the slanted aperture 116 of the plate 104. FIG. 5C is a top view of the slanted aperture 116 in absence of the bone screw 120. The slanted aperture 116 is comprised of a smooth countersunk surface 160 and teeth 164 that are configured to slidably engage with the inferior end 136 of the bone screw 120. The teeth 164 are configured to allow passage of the distal threads 148 therebetween and capture the head portion 124 during tightening of the bone screw 120 into the target bone. The smooth countersunk surface 160 generally orients the bone screw 120 at an oblique angle relative to the plate 104, as shown in FIG. 5A. Although the oblique angle may range between substantially 35 degrees and 45 degrees, as stated hereinabove, it is to be understood that the bone screw 120 may be oriented with respect to the plate 104 at any angle that is suitable for compressing the adjacent bones to be fused, without limitation. Moreover, although in the embodiment illustrated in FIG. 5C, two of the teeth 164 are disposed within the slanted aperture 116, it should be understood that more or less than two of the teeth 164 may be incorporated into the slanted aperture without limitation.

The countersunk surface 160 and the teeth 164 cooperate with the maximal circumference 144 of the bone screw 120 to allow the head portion 124 to seat relatively deeply into the slanted aperture 116 such that a minimal portion of the head portion 124 remains extending above an upper surface 168 of the plate 104. Further, as shown in FIG. 5B, a raised portion 172 may be disposed around the slanted aperture 116 on an underside 176 of the plate 104. Similar raised portions 172 may be disposed around each of the fixation apertures 112, without limitation. Preferably, each of the raised portions 172 around the fixation apertures 112 has a thickness that is substantially the same as the thickness of the raised portion around the slanted aperture 116. The raised portions 172 are relatively thicker regions of the plate 104 that may be configured to provide structural support to the apertures 112, 116, as well as to generally reduce an area of contact between the plate 104 and the target bone.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A bone fusion assembly for compressing adjacent bones across a bone fusion site to encourage fusion thereof, comprising:
   an elongate member comprising a plate that includes one or more fixation apertures to receive fasteners that are configured to be coupled with the adjacent bones;
   a threaded fastener comprising a bone screw that includes a head portion and a shank, the bone screw being configured to traverse the bone fusion site; and
   a slanted aperture disposed in the plate and configured to receive the bone screw at a predetermined angle with respect to a plane of the plate, the slanted aperture comprising a smooth countersunk surface and one or more teeth configured to cooperate with the head portion to compress the adjacent bones.

2. The assembly of claim 1, wherein the predetermined angle is an oblique angle that is selected to direct the bone screw across the bone fusion site and compress the adjacent bones together.

3. The assembly of claim 2, wherein the predetermined angle ranges between substantially 35 degrees and substantially 45 degrees.

4. The assembly of claim 1, wherein the smooth countersunk surface and the one or more teeth are configured to slidably engage with an inferior end of the head portion during tightening of the bone screw into the adjacent bones.

5. The assembly of claim 1, wherein the smooth countersunk surface and the one or more teeth are configured to cooperate with a maximal circumference of the head portion, such that a minimal portion of the head portion remains extending above an upper surface of the plate.

6. The assembly of claim 5, wherein the maximal circumference is disposed between a superior end and an inferior end of the head portion.

7. The assembly of claim 1, wherein the shank is comprised of distal threads and a proximal smooth portion, the distal threads being configured to rotatably engage within a suitably sized hole drilled in the adjacent bones, and the proximal smooth portion being configured to pass through the bone with relatively little resistance.

8. The assembly of claim 7, wherein the head portion is comprised of a superior end and an inferior end, the superior end including a shaped opening configured to engagedly receive a tool suitable for driving the bone screw into the suitably sized hole, and the inferior end being configured to be received within the slanted aperture such that the head portion countersinks within the slanted aperture and presses the plate against a surface of the adjacent bones.

* * * * *